United States Patent [19]

Kincade et al.

[11] Patent Number: 5,554,595
[45] Date of Patent: * Sep. 10, 1996

[54] SELECTIVE REGULATION OF B LYMPHOCYTE PRECURSORS BY HORMONES

[75] Inventors: Paul W. Kincade, Oklahoma City; Kay L. Medina, Moore, both of Okla.

[73] Assignee: Oklahoma Medical Research Foundation, Oklahoma City, Okla.

[*] Notice: The portion of the term of this patent subsequent to Apr. 7, 2014, has been disclaimed.

[21] Appl. No.: 321,156

[22] Filed: Oct. 11, 1994

Related U.S. Application Data

[63] Continuation of Ser. No. 44,280, Apr. 7, 1993, abandoned.
[51] Int. Cl.$^6$ .................. C07K 14/575; C07K 14/59; A61K 31/56; A61K 38/24
[52] U.S. Cl. .................. 514/21; 514/177; 514/182; 514/841; 514/843; 530/399; 530/850; 530/851; 530/852; 530/853; 530/854
[58] Field of Search .................. 514/841, 843, 514/177, 182, 21; 530/399, 850, 851, 852, 853, 854

[56] References Cited

U.S. PATENT DOCUMENTS

| | | | |
|---|---|---|---|
| 4,078,060 | 3/1978 | Benson et al. | 514/177 |
| 4,383,993 | 5/1983 | Hussain et al. | 514/177 |
| 4,701,450 | 10/1987 | Kelder et al. | 514/177 |
| 4,762,717 | 8/1988 | Crowley | 424/425 |
| 4,885,290 | 12/1989 | Asano et al. | 514/182 |
| 4,894,373 | 1/1990 | Young | 514/239.2 |
| 4,900,734 | 2/1990 | Maxson et al. | 514/171 |

OTHER PUBLICATIONS

Nikolevich et al. "Major Reproduction Hormones as Regulators of Cell-to-Cell Interactions in Humoral Immune Responses" Brain, Behav. Immun. 5 149–161 1991.

Kotani et al. "Effects of Estrogen on the Lymphoid Regeneration & Immune Response In Irradiated & Marrow-Reconstruction Mice" Acta Anat 105 298–1979.

Gray. "Hormones In Blood" 148–149 1983.

Chakraborty et al. "Effects of Long Term Treatment With Estadiol Or Clamiphene Citrate on Bone Maintenance, & Pituitary & Uterine Weights In Ovariectomized Rats" J Steroid Biochem Mol Biol 40 725–1991.

Abboud, S. L., C. R. Bethel, and D. C. Aron, "Secrection of Insulinlike growth factor 1 and insulinlike growth factor-binding proteins by murine bone marrow stromal cells," *J. Clin. Invest.* 88, pp. 470 (1991).

(List continued on next page.)

*Primary Examiner*—Michael G. Wityshyn
*Assistant Examiner*—Nancy J. Degen
*Attorney, Agent, or Firm*—Arnall Golden & Gregory

[57] ABSTRACT

Based on the discovery that normal pregnant mice have a striking reduction in committed precursors of B lymphocytes, which could be documented in mice as early as day 6 of gestation, when IL-7 responding colony forming cells were reduced as much as two-thirds of normal levels, it has been determined that estrogen and other hormones elevated in pregnancy induce a specific modulation of lymphocyte formation during pregnancy and lactation. It is therefore possible to immunomodulate in a specific manner an animal by administration of hormones elevated during pregnancy, such as estrogen and estrogen-like compounds, or antagonists of estrogen. This has potential in the treatment of a number of disorders, especially those found in very high percentages of women as compared with men, such as many of the autoimmune disorders, as well as in immune tolerance during pregnancy, cyclic neutropenia, and osteoporosis. There are also implications in culture of mammalian cells, since many of the culture medias include a dye such as phenol red as a pH indicator, which has estrogen-like properties, and animal sera which may not provide appropriate numbers and concentrations of hormones and therefore is not as beneficial for culture of cells which have responses similar to the lymphocytes.

4 Claims, 3 Drawing Sheets

OTHER PUBLICATIONS

Allman, D. M., S. E. Ferguson and M. P. Cancro, "Peripheral B cell maturation I. Immature peripheral B cells in adults are heat–stable antigen$^{hi}$ and exhibit unique signaling characteristics," *J. Immunol.*, vol. 149, p. 2533 (1992).

Aspinall, R. L., R. K. Meyer, and M. A. Rao, "Effect of varios steroids on the development of the bursa fabricilli in chick embryos," *Endocrin*, vol. 68, pp. 944 (1961).

Barr, I. G., et al., "Dihydrotestosterone and estradiol deplete corticonsensitive thymocytes lacking in receptors for these hormones," *J. Immunol.*, vol. 128, pp. 2825 (1982).

Calzolari, A. "Recherches experiments sur un rapport probable entre la fonction du thymus et celle des testicules," *Arch. Ital. de Biol.*, vol. 30, pp. 71 (1988).

Dardenne, M., P. A. Kelly, J–F, Bach. and W. Savino. "Identification and functional activity of prolactin receptors in thymic epithelial cells," *Proc. Natl. Acad. Sci. U.S.A.*, vol. 88, pp. 9700 (1991).

Dardenne, M. W. Savino, M–C, Gagnerault, T. Itoh, and J–F, Bach, "Neuroendocrine control of thymic hormonal production. I. Prolactin Stimulates in vivo and in vitro the production of thymulin by human and murine thymic epithelial cells," *Edocrin.* vol. 125, pp. 3 (1989).

Dougherty, T. F. "Effect of hormones on lymphatic tissue," *Physiol. Rev.* vol. 32, pp. 379 (1952).

Ehlich, A., et al., "Immunoglobulin heavy and light chain genes rearrange independantly at early stages of B cell development," *Cell*, vol. 72, p. 695 (1993).

Forsberg, J–G, "Short–term and long–term effects on lymphoid tissues and lymphoid cells with some remarks on the significance for carcinogenesis," *Arch. Toxicol.*, vol. 55, p. 79 (1984).

Forster, I., P. Viera, and K. Raiesky, "Flow cytomeric analysis of cell proliferation dynamics in the B cell compartment of the mouse," *Int. Immunol.*, vol. 1, p. 321 (1989).

Freitas, A. A. and B. B. Rocha, "Lymphocyte lifespans; Homeostasis selection and competition," Immunol. Today, vol. 14, pp. 25 (1993).

Fulci, F., "Die restitutionsfahigkeit des thymus der saugetiere nach der schwangershcaft," Zentrallbl. Allg. Pathol. vol. 24, pp. 968 (1913).

Girasole, G., et al., "17–β–estradiol inhibits interleukin–6 production by bone marrow–derived stromal cells and osteoblasts in vitro: A potential mechanism for the antiosteoporotic effect of estrogens," *J. Clin. Invest.*, vol. 89, pp. 883 (1992).

Glick, B. and C. Sadler, "The elimination of the bursa of fabricius and reduction of antibody production in birds from eggs dipped in hormone solutions," *Poult. Sci.*, vol. 40, pp. 185 (1961).

Hardy, R. R., et al., "Resolution and characterization of pro–B and pre–pro–B cell stages in normal mouse bone marrow," *J. Exp. Med.*, vol. 173, p. 1213 (1991).

Hayashi, S–I., et al, "Stepwise progression of B lineage differentiation supported by Interleukin 7 and other stromal cell molecules," *J. Exp. Med.*, vol. 171, pp. 1683 (1990).

Hayashi, et al., "Differential Effects of TGF–β1 on Lymphohemopoiesis in Long–Term Bone Marrow Cultures," *Blood*, vol. 74(5), pp. 1711–1717 (1989).

Holmdahl, R., "Estrogen exaggerates lupus but suppresses T–cell–dependent autoimmune disease," *J. Autoimmun.*, vol. 2, p. 651 (1989).

Hooghe, R., et al., "Growth hormone and prolactin are paracrine growth and differentiation factors in the haempietic system," *Immunology Today*, vol. 14, p. 212 (1993).

Ishihara, K., et al., "B29 gene complex with immunoglobulins on B lymphocytes," *Proc. Natl. Acad. Sci. USA*, vol.89, pp. 633 (1992).

Ito. T. and T. Hoshino, "Studies of the influences of pregnancy and lactation on the thymus in the mouse," *Zietschrift fur Zellforshung*, vol. 57, p. 667 (1962).

Jacob, J. and G. Kelsoe, "In situ studies of the primary immune response to (4–hydroxy–3–nitrophenyl) acetyl, II, A common clonal origin for periarteriolar lymphoid sheath–associated foci and germinal centers," *J. Exp. Med.*, vol. 176, pp. 679 (1992).

Jungers, P., et al., "Influence of oral contraceptive therapy on the activity of systemic lupus erythematosus," *Arthritis Rheum.*, vol. 25, pp. 618 (1982).

Jungers, P., et al., "Influence of oral contraceptive therapy on the activity of systemic lupus erythematosus," *Arthritis Rheum.*, vol. 25, p. 618 (1982).

Jyonouchi, H., et al., "Age–dependant deficiency of B lymphocyte lineage precursors in NZB mice," *J. Exp. Med.*, vol. 155, p. 1665 (1982).

Jyonouchi, H., P. W. Kincade, R. A. Good, and M. E. Gershwin, "B lymphocyte lineage cells in newborn and very young NZB mice, pp. Evidence for regulatory disorders affecting B cell formation," *J. Immunol.*, vol. 131, pp. 2219 (1983).

Jyonouchi, H., P. W. Kincade, "Precocious and enhanced functional maturation of B lineage cells in New Zealand Black mice during embryonic development," *J. Exp. Med.*, vol. 159, p. 1277 (1984).

Kincade, P. W., "Experimental models for understanding B lymphocyte formation," *Adv. Immunol.*, vol. 41, p. 181 (1987).

Kincade, P. W., "Molecular interactions between stromal cells and B precursors," *Semin. Immunol.*, vol. 3, p. 379 (1991).

Kincade, P. W., et al., "Antigens displayed on murine B precursors," *J. Immunol.*, vol. 127, pp. 2262 (1981).

Kincade, P. W., P. Ralph, and M. A. S. Moore, "Growth of B–lymphocyte clones in semisolid culture is mitogen dependant," *J. Exp. Med.*, vol. 143, p. 1265 (1976).

Landreth, K. S., et al., "Phenotypic and functional characterization of murine B lymphocyte precursors isolated from fetal and adult tissues," *J. Immunol.*, vol. 131, pp. 572–580 (1983).

Landreth, K. S., R. Narayanan, and K. Dorshkind, "Insulin––like growth factor–1 regulates pro–B cell differentiation," *Blood.* vol. 80, p. 1207 (1992).

Landreth, K. S., et al., "Regulation of human B lymphopoiesis; *Effect of a urinary activity associated with cyclic neutropenia,"* *J. Immunol.*, vol. 134, p. 2305 (1985).

Le Douarin, N. M., G. Michel, and E–E, Baulieu "Studies of testosterone–induced involution of the bursa of fabricius," *Dev. Biol.*, vol. 75, p. 288 (1980).

Lee, G., et al., "Normal B cell precursors responsive to recombinant murine IL–7 and inhibition of IL–7 activity by transforming growth factor–β," *J. Immunol.*, vol. 142, p. 3875 (1989).

McMurray, R., et al., "Prolactin influences autoimmune disease activity in the female B/W mouse," *J. Immunol.*, vol. 147, p. 3780 (1991).

Medina, K. L., et al., "Suppression of B Lymphopoesis During Normal Pregnancy," *J. Exp. Med.*, vol. 178, pp. 1507–1515 (Nov. 1993).

Meyer, R. K., M. A., Rao, and R. L. Aspinall "Inhibition of the development of the bursa of fabricus in the embryos of the common fowl by 19–Nortestosterone," *Endocrin*, vol. 64, p. 890 (1959).

Mountz, J., "Animal models of systemic lupus erthematosus and Siogren's syndrome," *Curr. Opin. Rheumatol.*, vol. 2, p. 740 (1990).

Mund. A., J. Simson, and N. Rothfield, "Effect of pregnancy on course of systemic lupus erthematosus," *JAMA*, vol. 183, p. 917 (1963).

Murphy, W. J., et al., "Immunologic and hematologic effects of neuroendocrine hormones," *J. Immunol.*, vol. 148, p. 3799 (1992).

Norton, J. M. and C. R. Wira, "Dose–related effects of the sex hormones and cortisol on the growth of the bursa of fabricus in chick embryos," *J. Steroid Biochem.*, vol. 8, p. 985 (1977).

Novotny, E. A., et al., "Analysis of thymocyte subpopulations following treatment with sex hormones," *Clin. Immunol. Immunopathol.*, vol. 28, p. 205 (1983).

Ogawa, M. Y. et al., "Expression and function of c–kit in hemopoietic progenitor cells," *J. Exp. Med.*, vol. 174, p. 63 (1991).

Okuyama, R., et al., "Estrogen administration activates extrathymic T cell differentiation in the liver," *J. Exp. Med.*, vol. 175, p. 661 (1992).

Opstelten, D., and D. G. Osmond, "Regulation of pre–B cell proliferation in bone marrow: Immunofluorescent stathmokinetic studies of cytoplasmic 1–chain bearing cells in anti–IgM treated, hematologically deficient mutant and antigen stimulated mice," *Eur. J. Immunol.*, vol. 15, p. 599 (1985).

Osmond, D. G., "The turnover of B–cell populations," *Immunol. Today*, vol. 14, p. 34 (1993).

Osmond, D. G., S. Priddle, and S. Rico–Vargas, "Proliferation of B cell precursors in bone marrow of pristane–conditioned and malaria–infected mice: Implications for B cell oncognesis," *Curr. Top. Microbiol. Immunol.*, vol. 166, p. 149 (1990).

Osmond, D. G., "B cell development in the bone marrow," *Semin. Immunol.*, vol. 2, p. 173 (1990).

Osmond, D. G., et al., "Dynamics and localization of early B–lymphocyte precursor cells (Pro–B cells) in the bone marrow of scid mice," *Blood*, vol. 79, p. 1695 (1992).

Park, Y. H. and D. G. Osmond, "Phenotype and proliferation of early B lymphocyte precursor cells in mouse bone marrow," *J. Exp. Med.*, vol. 165, p. 444 (1987).

Park, Y–H, and D. G. Osmond, "Dynamics of early B lymphocyte precursor cells in mouse bone marrow: Proliferation of cells containing terminal deoxynucleotidyl transferase," *Eur. J. Immunol.*, vol. 19, p. 2139 (1989).

Phuc, L. H., M. Papiernik, S. Berrih, and D. Duval, "Thymic involution in pregnant mice, I. Characterization of the remaining thymocyte subpopulations," *Clin. Exp. Immunol.*, vol. 44, p. 247 (1981).

Pietrangeli, C. E. and D. G. Osmond, "Regulation of B–lymphocyte production in the bone marrow: Role of macrophages and the spleen in mediating responses to exogenous," *Cell. Immunol.*, vol. 94, p. 147 (1985).

Pope, R. M., "Immunoregulatory mechanisms present in the maternal circulation during pregnancy," *Bailliere's Clin. Rheumatol.*, vol. 4, p. 33 (1990).

Rodriguez–Tarduchy, G., et al., "Insulin–like growth factor–I inhibits apoptosis in IL–3–dependent hemopoietic cells," *J. Immunol.*, vol. 149, p. 535 (1992).

Russell, D. H., et al., "Neonatal administration of prolactin antiserum alters the development pattern of T–and B–lymphocytes in the thymus and spleen of BALB/c female mice," *Proc. Natl. Sci. USA*, vol. 85, p. 7404 (1988).

Screpanti, I., et al., "In vivo modulation of the distribution of thymocyte subsets: Effects of estrogen on the expression of different T cell receptor T cell receptor V beta families in CD–4, CD8–thymocytes," *Cell. Immunol.*, vol. 134, p. 414 (1991).

Screpanti, I., et al., "Steroid sensitivity of thymocyte subpopulations during intrathymic differentiation, Effects of 17 beta–estradiol and dexamethasone on subsets expressing T cell antigen receptor or IL–2 receptor," *J. Immunol.*, vol. 142, p. 3378 (1989).

Strasser, A., A. Rolink, and F. Melchers, "One synchronous wave of B cell development in mouse fetal liver changes at day 16 of gestation from dependance to independance of a stromal cell enviroment," *J. Exp. Med.*, vol. 170, p. 1973 (1989).

Sunblad, A., et al., "Normal serum immunoglubulins influence the numbers of bone marrow pre–B and B cells," *Eur. J. Immunol.*, vol. 21, p. 1155 (1991).

Szekeres–Bartho, J., "Endocrine regulation of the immune system during pregnancy," In *Immunology of Pregnancy*, G. Chauoat, editor. CRC Press, Inc., Boca Raton 151 (1993).

Thompson, Jr., E. A., "The effects of estradiol upon the thymus of the sexually immature female mouse," *J. Steroid Biochem.*, vol. 14, p. 167 (1981).

Witte, P. L., et al., "Relationships between B–lineage lymphocytes and stromal cells in long–term bond marrow cultures," *Eur. J. Immunol.*, vol. 17 p. 1473–1494 (1987).

Xenocostas, A., D. G. Osmond, and W. S. Lapp, "The effect of the graft–host reaction on B lymphocyte production in bone marrow of mice: Depressed genesis of early progenitors prior to μ heavy chain expression," *Transplantation*, vol. 51, p. 1089 (1991).

Nikolaj, K. N., et al., "Major Reproduction Hormones as Regulators of Cell–to–Cell Interactions in Humoral Immune Responses," 5 *Brain, Behavior, and Immunity*, 149–161 (1991).

Kotani, M., et al, "Effects of estrogen on the lymphoid regeneration and immune response in irradiated and marrow–reconstructed mice," 105 *Acta Anat.*, 298–308 (1979).

5,554,595

SELECTIVE REGULATION OF B LYMPHOCYTE PRECURSORS BY HORMONES

This is a continuation of application Ser. No. 08/044,280 filed on Apr. 7, 1993, now abandoned.

BACKGROUND OF THE INVENTION

The present invention is generally in the area of immunoregulation, and is particularly the selective hormone-mediated modulation of lymphocyte formation in bone marrow.

The formation of lymphocytes and other blood cells is a carefully regulated process that is essential for maintenance of a normal immune system. Lymphocytes responsible for antibody formation, B lymphocytes, are made in bone marrow. Another major category of lymphocytes, T lymphocytes, is made in the thymus. Together these lymphocytes are responsible for both the humoral (antibody) mediated immune response and the cell mediated immune response.

Studies of molecular regulators of B lymphopoiesis have focused on aspects that might be organ, i.e., bone marrow, specific. However, to date, no molecules have been found which are unique to that tissue.

There is a gradual atrophy of the thymus with age, but the mechanism through which this occurs is not known. It has also long been known that the thymus atrophies during pregnancy and regenerates after delivery. There is reason to believe that this phenomenon is regulated by hormones, because estrogen injections have been observed to cause similar thymus atrophy. However, the immune system is thought to function normally during pregnancy, that is, the host defense against pathogens is intact.

A better understanding of the influence of hormones on the humoral immune system is needed. This information may be relevant to maternal—fetal relationships during pregnancy and abnormalities involving them, as well as to the pathophysiologic mechanisms of autoimmune diseases such as systemic lupus erythematosus (SLE), which are commonly diagnosed or worsen during pregnancy. The same is true of diseases such as cyclic neutropenia, which may have a basis in hormonal dysfunction. An increased awareness of the effect of hormone administration may also help prevent iatrogenic disease or the side effects of hormones replacement therapy, such as in the treatment of osteoporosis. It may also be possible to utilize this basic information to manipulate immunologic tolerance and achieve immunosuppression, or alternatively, with hormone antagonists, to augment the humoral immune system. Moreover, methods for propagating lympho-hemopoietic progenitor cells and stem cells in culture might be improved by manipulation of hormone concentrations in cell culture medium.

It is therefore an object of the present invention to provide a method for immunomodulation through manipulation of specific classes of immune cells, especially B lymphocytes, by administration of compounds having an effect on the number of B lymphocyte precursors.

It is a further object of the present invention to provide methods and means for manipulation of B lymphocytes involved in autoimmune disorders, osteoporosis, and cyclic neutropenia.

It is another object of the present invention to provide methods and means to improve cell culture of bone marrow and stromal cells.

SUMMARY OF THE INVENTION

Based on the discovery that normal pregnant mice have a striking reduction in committed precursors of B lymphocytes, which could be documented in mice as early as day six of gestation, when IL-7 responding colony forming cells were reduced as much as two-thirds of normal levels, it has been determined that estrogen and other hormones elevated in pregnancy induce a specific down-regulation of B lymphocyte formation during pregnancy and lactation. This could also be induced by administration of specific hormones in animals that were not pregnant or lactating. Similar effects were observed with administration of progesterone, but only in combination with estrogen.

It is therefore possible to influence in a specific manner the immune system of an animal by administration of hormones such as estrogens, estrogen-like compounds, and related steroids. This has potential in the treatment of a number of disorders, especially those found in very high percentages of women as compared with men, such as many of the autoimmune disorders, as well as in immune tolerance during pregnancy, cyclic neutropenia, and osteoporosis. There are also implications in culture of mammalian cells, since many of the culture medias include a dye such as phenol red as a pH indicator, which has estrogen-like properties, and/or animal serum with nonphysiologic hormone concentrations and therefore may not be beneficial for culture of cells which have requirements similar to lymphocyte precursors.

BRIEF DESCRIPTION OF THE DRAWINGS

FIG. 2a are normal control mice. FIG. 2b is at 17 days gestation. FIG. 2c is at 18 days gestation. FIG. 2d is at term. Cells in upper right quadrant represent B lymphocytes. Cells in the upper left hand quadrant are B lineage precursor cells.

DETAILED DESCRIPTION OF THE INVENTION

Figure 1:
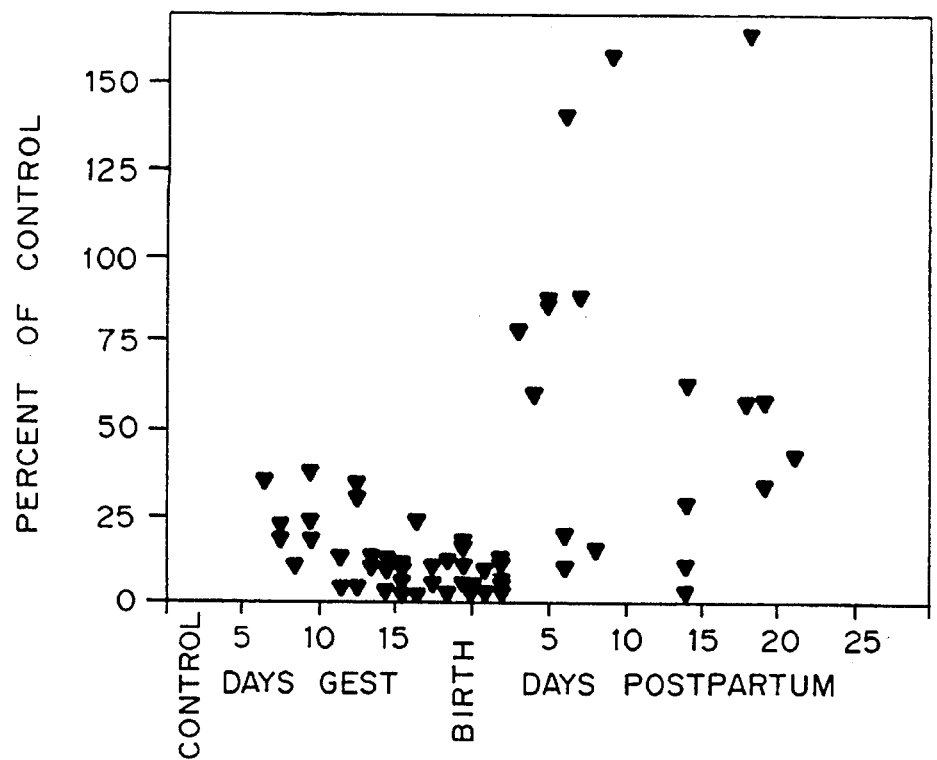
FIG. 1 is a graph of the percent of control of IL-7 responsive B lineage precursors versus days of gestation and days of postpartum for normal mice. Bone marrow cells were obtained from BALB/c mice at various stages of pregnancy and during the postpartum period and placed in semisolid agar with interleukin 7. The numbers of proliferating foci were determined after six days of culture.

It has been found that during pregnancy there is a drastic and selective decline in IL-7 responsive, CD45R+, sIgM− Pre-B cells in murine bone marrow. By term, numbers of these cells were 10% of normal. A phenotypic analysis revealed that B lineage precursors (CD45R$^+$,sµ$^-$) were correspondingly reduced as were early lymphocyte progenitors containing nuclear TdT. Thymus atrophy and an enrichment of CD3$^+$ cells is observed during pregnancy. Myeloid and erythroid cells in marrow were not obviously affected.

This observation could be effected by administration of estrogen-like hormones to normal female animals. Pellets containing various pregnancy-related hormones were implanted into normal female mice and examined two weeks later. The pregnancy-associated phenomenon was mimicked when normal, non-pregnant mice were implanted with 17β estradiol containing pellets. These findings indicate that hormones can specifically influence B lymphopoiesis.

Hormones that are useful to influence B lymphopoiesis.

Examples of hormones that are elevated during pregnancy include estrogen, progesterone, human chorionic gonadotropin (HCG), human placental lactogen, prolactin, and cortisol. Furthermore, it may be possible to achieve the same effect with agents such as gonadotropin releasing hormone (GNRH) which stimulate production of the same pregnancy hormones. All of these are available commercially from Sigma Chemical Co. (St. Louis, Mo.) and a variety of other suppliers. Agents such as RU 486, which inhibit progesterone action, and ICI 182,780, Zeneca Pharmaceuticals, which block estrogen responses may also be useful in this regard. The latter compound simulates estrogen withdrawal, without affecting the hypothalamic-pituitary axis. Another compound, tamoxifen, has both estrogen and anti-estrogen activities, but is species specific in some respects.

Compounds can also be useful which inhibit the endogenous production of these hormones, or compete with these hormones for cell surface receptors, thereby having an inhibitory or antagonistic effect.

Effect of Hormones on Cell Culture

Long term bone marrow culture (LTBMC) studies were performed to identify potential cellular targets of estrogen action and evaluate other effective hormones. Appropriate doses of estrogen and progesterone selectively inhibited formation of lymphoid, but not myeloid, cells in LTBMC. Addition of human chorionic gonadotropin (HCG) stimulated growth of the adherent layers in such cultures.

Hormones which were tried in this context include 17 beta estradiol (E2), progesterone, dehydroepiandrosterone (DHEA), DHEA sulphate, prolactin, and growth hormone. The hormones had no significant influence on growth of established lymphomyeloid cell lines, clonable pre-B cells or an IL-7 dependent pre-B cell clone. Thus, the effect of estrogens and HCG on lymphopoiesis may be indirect, or may be on a very early state in the B cell lineage. The possibility of an influence on stromal cells is being determined. However, studies with progesterone indicate that lymphocyte precursors may be directly affected by this hormone. Therapeutic Applications Autoimmune Disorders The specific action of hormones has not been elicited. However, there are a number of indications that hormones affect the function of mature antibody forming B cells and that hormones may participate in diseases involving these cells. For example, the disease systemic lupus erythrymatosis (SLE) is ten times more prevalent in women, and is often first diagnosed or exacerbated during pregnancy. Experiments with autoimmune prone mice, New Zealand Black (NZB), implicate sex hormones in such diseases. Previous studies showed that B lymphocyte precursors in this strain of animals appear at an elevated rate during embryonic life, and decline at an accelerated rate during postnatal life. This may reflect an abnormal production of, or responsiveness to, hormones, as reported by Jyonouchi, et al., *J. Exp. Med.* 159:1277 (1984) and Jyonouchi, et al., *J. Exp. Med.* 155:1665 (1982). There have been a number of studies indicating that there is endocrine participation in autoimmune manifestations in this model. Studies have also been conducted with patients who have a rare form of immunodeficiency disease, as described by Engelhard, et al., *Proc. Natl. Acad. Sci.* 80:5734 (1983). Boys with cyclic neutropenia have a deficiency of neutrophil granulocytes at regular intervals. It has been found that numbers of pre-B cells in bone marrow increase precisely when numbers of myeloid cells decline. This abnormality may be related to hormonal dysfunction.

Accordingly, it is believed that administration of hormones, or hormone inhibitors, hormone eliciting agents, hormone antagonists, and combinations thereof to women that have autoimmune disorders can be used selectively to immunomodulate these disorders. This presents a very favorable alternative to the steroid therapy now in use. Moreover, diagnostic procedures for immune deficiencies, autoimmune diseases in both men and women, leukemias and other disorders might be greatly improved.

Treatment of Bone Marrow Transplants

Steroid hormones may be important regulators of normal lymphopoiesis. Senescence of the immune system could in part be related to hormonal influences on lymphocyte precursor numbers. As a result, knowledge of the influence of hormones on lymphopoiesis should be useful for designing conditions favorable for long term cultures. It should also be useful in treatment of bone marrow harvested for transplantation, both before and after transplantation. For example, hormones may modulate expression and/or function of cell adhesion molecules in bone marrow, which would result in mobilization of stem cells or committed precursors into the blood stream. These could then be conveniently collected and used for bone marrow transplantation. It might also be beneficial to treat bone marrow donors with certain hormones before transplantation in order to deplete potential recipient reactive lymphocytes or modify the homing behavior of stem cells in recipients.

Iatrogenic Effects of Hormone Therapy

Estrogens are currently used to prevent osteoporosis. Compounds such as tamoxifen, which has estrogenic-like activity, are employed for breast cancer therapy. A better understanding of the effects of such agents on precursor cells in bone marrow may be relevant to identifying potential side effects and developing strategies for modifying the same.

Applications in Cell Culture

It has long been an objective to establish and optimize conditions for maintenance of lympho-hemopoietic progenitors and stem cells in culture. Some success has been achieved in this regard with bone marrow cells from mice, but it is generally more limited with human cells. If it were possible to maintain and expand human stem cells in culture, this would provide a new approach to bone marrow transplantation and facilitate introduction of new genes.

Sufficient attention has not been paid to the role of hormones in lympho-hemopoiesis and titration of various hormones in culture media might result in improved survival and/or differentiation of particular cell types.

It has been demonstrated that hormones can both stimulate and inhibit proliferation and growth of selective groups of lymphocytes, both in vitro and in vivo. Therefore, it should be possible to improve culture of these cells either by administration of the hormones that stimulate growth or depletion of compounds having a estrogenic or progesteronic effect, such as phenol red, a dye commonly used as a pH indicator which has estrogenic activity, or animal sera containing non-physiologic concentrations of hormones.

Accordingly, culture medium formulations which are either serum free, or contain low concentrations of estrogen (fetal calf serum depleted by charcoal extraction or freon treatment) and no phenol red, should be utilized. A variety of pregnancy related and other hormones can be titrated into cultures of human or murine bone marrow with this medium to determine which ones stimulate or depress cell growth. Hormones to be tested in this way include estrogens, progesterone, human chorionic gonadotropin (HCG), human placental lactogen, growth hormone, follicle stimulating hormone (FSH), luteinizing hormone (LH), dihydrotestosterone, vitamin D3, prolactin, and glucocorticoids. Doses will range from $10^{-10}$ to $10^{-6}$ M final concentrations.

The present invention will be further understood by reference to the following non-limiting examples.

EXAMPLE 1

Selective suppression of B lineage precursors in pregnant animals

The incidence of B lymphocyte precursors in bone marrow dramatically declines during pregnancy and, depending on whether lactation is permitted, regenerates after delivery. Precursors of other types of blood cells are present in either normal, or slightly elevated numbers during pregnancy.

B lymphocyte lineage precursors which are responsive to interleukin 7 from pregnant mice were assayed with a semisolid agar cloning technique, as reported by Lee, et al., *J. Immunol.* 142:3875 (1989). FIG. 1 is a graph of the percent of control of IL-7 responsive B lineage precursors versus days of gestation and days of postpartum for normal mice. Bone marrow cells were obtained from BALB/c mice at various stages of pregnancy and during the postpartum period and placed in semisolid agar with interleukin 7. The numbers of proliferating foci were determined after six days of culture.

The results show a significant depression in numbers of B lineage precursor cells but not mature B cells. Numbers of responding cells in maternal bone marrow were very reduced within 6 days of gestation and averaged about 10% of normal throughout pregnancy. These regenerated after delivery, and did so most dramatically when offspring were removed from the mother at the time of birth.

Figure 2A:
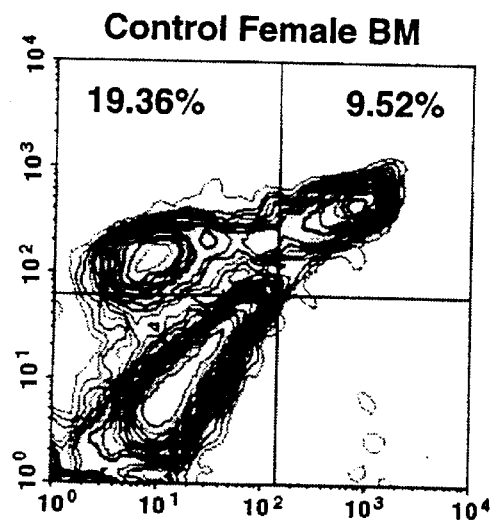
FIGS. 2a, 2b, 2c, and 2d show by flow cytometry the analysis of B lineage precursors in bone marrow of control and pregnant mice.
Figure 2B:
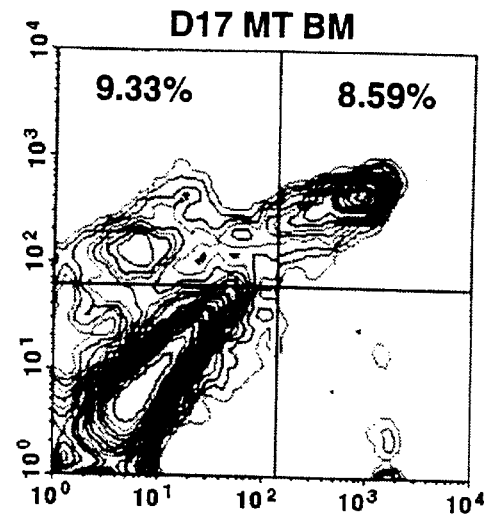
Figure 2C:
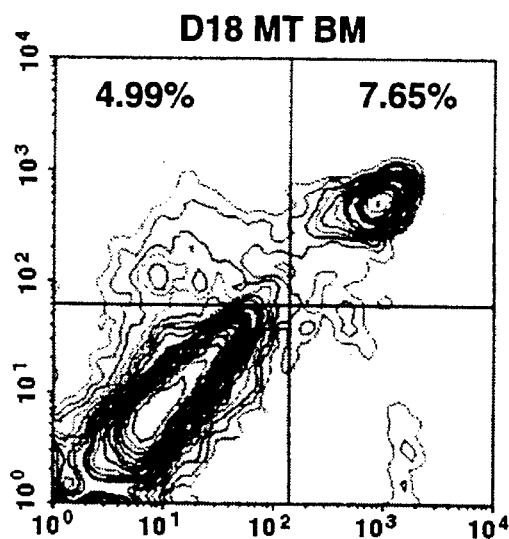
Figure 2D:
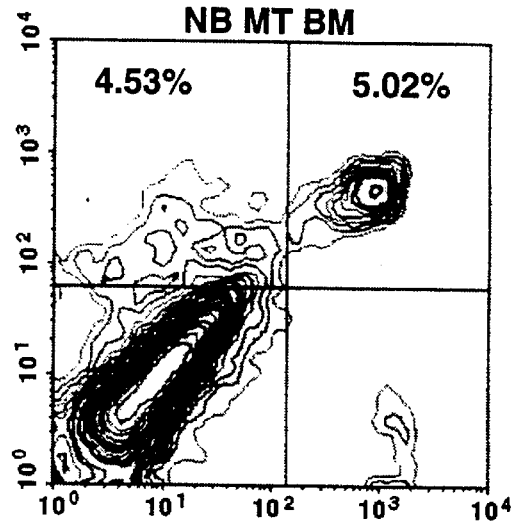

FIGS. 2a, 2b, 2c, and 2d show by flow cytometry the analysis of B lineage precursors in bone marrow of control and pregnant mice. FIG. 2a are normal control mice. FIG. 2b is at 17 days gestation. FIG. 2c is at 18 days gestation. FIG. 2d is at term. Single cell suspensions of bone marrow were prepared and stained with an FITC labeled antibody to IgM (Southern Biotechnology Assoc., Birmingham, Ala.). The same preparations were treated with a biotin labeled monoclonal antibody (14.8) to murine CD45RA. This reagent was then detected with an additional step, where the cells were stained with phycoerythrin (PE) labeled streptavidin. Simultaneous two color analysis was then performed on individual cells with a BD FACScan flow cytometer. Cells in upper right quadrants represent B lymphocytes. Their numbers did not change significantly during pregnancy. In contrast, there was a marked decline in numbers of B cell precursors in the upper left hand quadrant at 17 and 18 days gestation, and at term.

Figure 3:
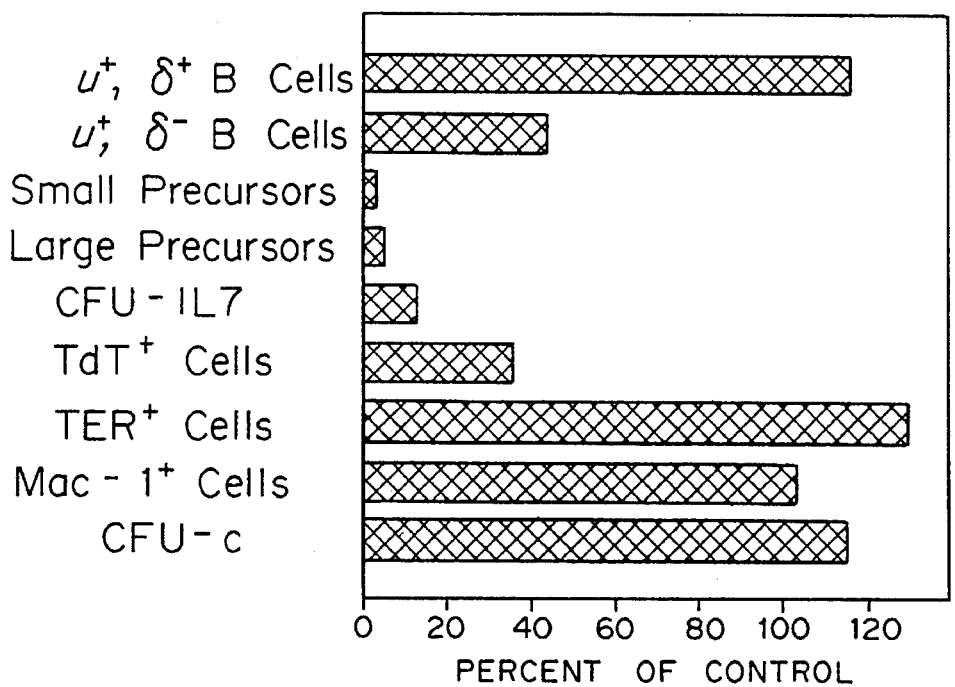
FIG. 3 is a bar graph of the effects of pregnancy on bone marrow cells as a percent of control. Cell types are µ+, delta B cells; µ+, delta- B cells, small precursors; large precursors; CFU-IL7; TdT+ cells; TER+ cells; Mac-1+ cells; and CFU-c.

Other assays were then used to enumerate cells with B lymphocyte precursor characteristics. FIG. 3 is a bar graph of the effects of pregnancy on bone marrow cells as a percent of control. Cell types are μ+, delta B cells; μ+, delta- B cells, small precursors; large precursors; CFU-IL7; TdT+ cells; TER+ cells; Mac-1+ cells; and CFU-c. The only significant declines found thus far are in cells identified as precursors of B lineage lymphocytes. Early cells in this series contain the enzyme terminal deoxynucleotidyl transferase (TdT) and they give rise to large precursors, which are also detectable with the IL-7 cloning assay. Small pre-B represent the immediate precursors of B cells. Mature and immature forms of the latter are discriminated on the basis of IgD expression.

Cells containing the enzyme terminal deoxynucleotidyl transferase (TdT) were depressed in pregnant animals, as were cells expressing markers typical of large and small pre-B cells. These markers include CD45RA, CD43, heat stable antigen, the absence of surface immunoglobulin and the presence of cytoplasmic mu chains of immunoglobulin. Numbers of mature B cells, as determined by immunofluorescence and flow cytometry to bear surface IgM and IgD, in bone marrow and other tissues were not depressed. Moreover, bone marrow cells with characteristics of erythroid and myeloid cells were present in normal, or slightly elevated numbers. These cells were assessed with a cloning assay for granulocyte —macrophage progenitor cells (CFU-c assay) and immunofluorescence with TER 119 (provided from Dr. T. Hina, Kyoto, Japan) and Mac-1 monoclonal antibodies (obtained from the American Type Culture Collection, Rockville, Md.).

These results are in accordance with observations that the immune system functions normally during pregnancy in defense against pathogens. Most of the mature B lymphocytes are probably memory cells which have been involved in previous immune responses and which may survive for years. It is possible that the precursor cells are suppressed during pregnancy to avoid rejection of the fetus, but that over a long time suppression of new B lymphocytes would lead to the immune system becoming less well regulated. This could be a factor in the higher frequency of diagnosis of autoimmune disorders in pregnant women.

EXAMPLE 2

Hormone induced suppression of B lineage precursor cells

To determine if hormones which normally rise during pregnancy are responsible for this effect on bone marrow, normal female mice were implanted with hormone containing pellets and studied at intervals thereafter. Normal BALB/c female mice were used for all studies and were at least 8 weeks old. Pellets containing placebo or graded concentrations of hormones, were obtained from Innovative Research of America, Toledo, Ohio. Three estrogens: estrone, estradiol, and estriol, alone or in combination with progesterone, were tested.

Figure 4A:
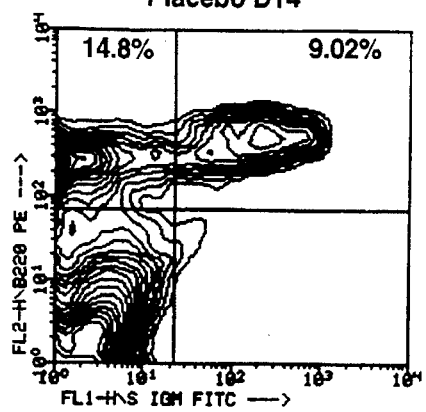
FIGS. 4a, 4b, 4c, 4d and 4e are the analysis by flow cytometry of the dose dependent depression of B lineage precursors following the implantation of estrogen containing pellets in normal mice. Normal BALB/c female mice were given pellets containing placebo (FIG. 4a) or 2.5 mg of β17 estradiol (FIG. 4b), estriol (FIG. 4c), estrone (FIG. 4d), or DHEA (FIG. 4e). Bone marrow samples were collected after two weeks of treatment and analyzed as described with reference to FIGS. 2a–d.
Figure 4B:
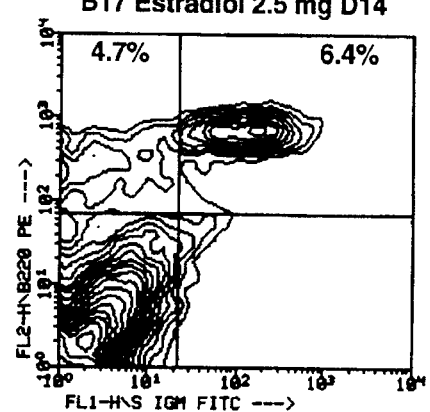
Figure 4C:
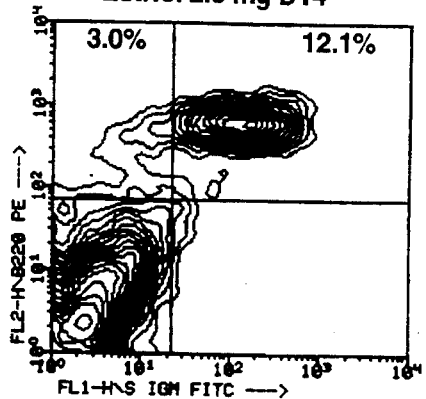
Figure 4D:
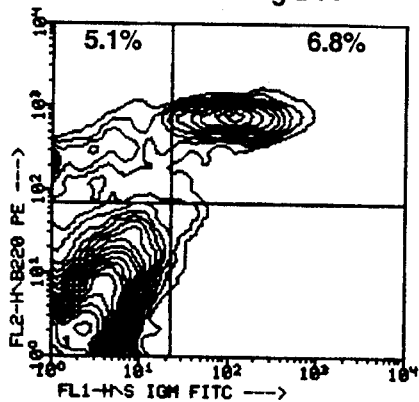
Figure 4E:
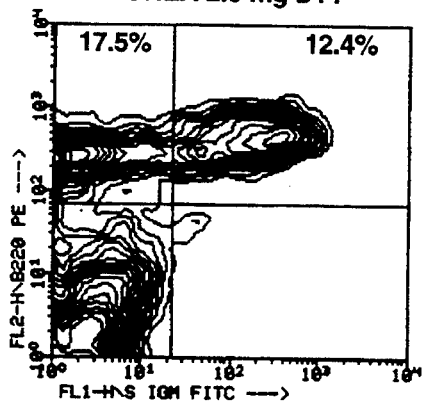

FIGS. 4a, 4b, 4c, 4d and 4e are the analysis by flow cytometry of the dose dependent depression of B lineage precursors following the implantation of estrogen containing pellets in normal mice. Normal BALB/c female mice were given pellets containing placebo (FIG. 4a) or 2.5 mg of β17 estradiol (FIG. 4b), estriol (FIG. 4c), estrone (FIG. 4d), or DHEA (FIG. 4e). Bone marrow samples were collected after two weeks of treatment and analyzed as described with reference to FIGS. 2a–d.

Results are shown numerically in Table I.

TABLE I

| | Selective Depletion of B Cell Precursors by Estrogen Treatment*. | | | | |
|---|---|---|---|---|---|
| Assay | placebo | estradiol | estriol | estrone | DHEA |
| pre-B | 33 ± 5 | 3 ± 1 | 0 | 3 ± 3 | 20 ± 3 |
| myeloid | 70 ± 15 | 103 ± 12 | 126 ± 42 | 101 ± 23 | 143 ± 17 |
| B cells | 44 ± 11 | 75 ± 20 | 174 ± 40 | 45 ± 14 | 74 ± 5 |

*Normal adult female BALB/c mice were implanted with pellets containing placebo, or 2.5 mg of the indicated estrogens, or the androgen dehydroepiandrosterone (DHEA). Bone marrow was harvested after two weeks of treatment and cells ($5 \times 10^4$) were placed in semisolid agar cloning assays for pre-B cells (cultures containing IL-7), myeloid progenitors (cultures containing CSF), and B cells (cultures containing LPS).

Estrogen pellets containing 2.5 mg of hormone were effective at simulating pregnancy and caused a selective depletion of B lymphocyte precursors in bone marrow. Progesterone pellets, when used alone, had no effect. However, preliminary experiments indicate that progesterone may enhance suppression mediated by estrogen when the two hormones are used together.

EXAMPLE 3

Effect of hormone addition in cell culture

Experiments were then done to determine if estrogens influence the formation of lymphocytes in a long term bone marrow culture model. Two systems were used. The first, which supports growth of B lymphocyte lineage cells, was sensitive to addition of estradiol. In contrast, a second type of culture, which maintains growth of non-lymphoid (myeloid) cells in vitro, was unaffected by the same hormone.

Long term bone marrow cultures were then set up under Whitlock-Witte (lymphoid) or Dexter culture conditions, as described in detail by Witte, et al., *Eur. J. Immunol.* 17:1473 (1987), and Hayashi, et al., *Blood* 74:1711 (1989), and hormones were added to certain groups of culture flasks. Some hormones, such as progesterone, had no effect on either type of culture. Estrogen suppressed lymphocyte formation in culture, but had no effect on growth of myeloid cells which have reached this stage of maturation.

These results indicate that bone marrow is a direct target of hormone action and that formation of a discrete population of blood cells is selectively influenced.

Hormones are now being added to co-cultures of cloned stromal cell lines and limiting numbers of normal, partially separated bone marrow cells. Estrogens depress numbers of clonally proliferating cells in this model, indicating that this assay may contain a sufficiently early lymphocyte precursor which is estrogen sensitive and/or that stromal cell functions are subject to regulation by this hormone.

EXAMPLE 4

Effect of hormones on calcium deposition by stromal cells

An interesting, and potentially important effect, was noted with another hormone. Human chorionic gonadotropin (HCG) caused more rapid than normal growth of cells in the adherent layer. One interesting result has been obtained with HCG, which seems to cause the deposition of calcium by stromal or other cells in the adherent layer in a long term bone marrow culture. It may be that this hormone induces osteoblast like differentiation in stromal cells, a finding which could have implications for attempts to accelerate or control bone formation. Stromal cells may respond to estrogens as a result of interaction with regulatory cytokines. For example, estrogen might induce production of interleukin I, or TGF-β which are known inhibitors of B lymphocyte formation. This could be indirect, for example, if estrogen induced cathepsin D, which in turn activated TGF-β via proteolytic action on a latent form. There is also reason to suspect that hormones may regulate the expression and/or function of cell adhesion molecules, such that retention of immature cells in marrow is affected.

EXAMPLE 5

Administration to animals of an estrogen antagonist to determine its effect on B lymphocyte formation A pure estrogen antagonist is being tested for its effects on B lymphocyte formation. The drug, known as ICI 182,780, will be provided for investigational use by Zeneca Pharmaceuticals in England. The study is to determine if estrogen withdrawal, which can be achieved in animals or culture with this drug, results in augmented lymphocyte formation. The same drug, along with estrogen pellets, can be used in an attempt to manipulate the bone marrow of autoimmune prone NZB mice.

Modifications and variations of the present invention will be obvious to those skilled in the art from the foregoing detailed description. Such modifications and variations are intended to come within the scope of the following claims.

We claim:

1. A method for modulating production of committed mammalian B lymphocyte precursor cells in a culture of cells containing B lymphocyte precursor cells and mature B lymphocytes comprising exposing the mix of cells to a hormone selected from the group consisting of hormones elevated during pregnancy, synthetic analogues of the hormones elevated during pregnancy, eliciting agents of the hormones elevated during pregnancy, and antagonists of the hormones elevated during pregnancy, in an amount effective to alter selectively the production of mammalian B lymphocyte precursor cells by proliferation or differentiation as compared with proliferation of mature B lymphocytes.

2. The method of claim 1 wherein the hormone is selected from the group of natural and synthetic hormones consisting of estrogen, estrone, estradiol, estriol, progesterone, and combinations thereof and the amount is effective to inhibit selectively the production of mammalian B lymphocyte precursor cells compared to mature B lymphycytes.

3. The method of claim 1 wherein the hormone is selected from the group consisting of chorionic gonadotropin, hormone eliciting agents, hormone antagonists, and combinations thereof and the amount is effective to manipulate selectively the production of mammalian B lymphocyte precursor cells compared to mature B lymphycytes.

4. The method of claim 1 wherein the cells are bone marrow cells in culture.

* * * * *

UNITED STATES PATENT AND TRADEMARK OFFICE
CERTIFICATE OF CORRECTION

PATENT NO. : 5,554,595
DATED : September 10, 1996
INVENTOR(S) : Paul W. Kincade and Kay L. Medina It is certified that error appears in the above-indentified patent and that said Letters Patent is hereby corrected as shown below:

Column 1 Line 7, insert the following information:

The United States Government has certain rights in this invention by virtue of National Institute of Health's grant AO 496507 to Paul Kincade.

Signed and Sealed this

Eighteenth Day of March, 1997

Attest:

BRUCE LEHMAN

Attesting Officer

Commissioner of Patents and Trademarks